United States Patent [19]

L'Esperance, Jr.

[11] Patent Number: 4,798,204

[45] Date of Patent: * Jan. 17, 1989

[54] METHOD OF LASER-SCULPTURE OF THE OPTICALLY USED PORTION OF THE CORNEA

[75] Inventor: Francis A. L'Esperance, Jr., Englewood, N.J.

[73] Assignee: LRI L.P., New York, N.Y.

[ * ] Notice: The portion of the term of this patent subsequent to May 19, 2004 has been disclaimed.

[21] Appl. No.: 80,398

[22] Filed: Jul. 29, 1987

Related U.S. Application Data

[63] Continuation-in-part of Ser. No. 049,333, May 13, 1987, which is a continuation-in-part of Ser. No. 748,358, Jun. 24, 1985 Pat. No. 4,665,913, Ser. No. 891,169, Jul. 31, 1986, and Ser. No. 891,285, Jul 31, 1986 Pat. No. 4,732,148, said Ser. No. 748,358 Pat. No. 4,665,913, is a continuation-in-part of Ser. No. 552,983, Nov. 17, 1983, abandoned, said Ser. No. 891,169, is a continuation-in-part of Ser. No. 780,335, Sep. 26, 1985, abandoned, which is a continuation-in-part of Ser. No. 740,276, Jun. 3, 1985, abandoned, which is a continuation-in-part of Ser. No. 552,983, abandoned, which is a continuation-in-part said Ser. No. 891,285 Pat. No. 4,732,148, is a continuation-in-part of Ser. No. 778,801, Sep. 23, 1985, abandoned, which is a continuation-in-part of Ser. No. 742,225, Jun. 6, 1985, abandoned, which is a continuation-in-part of Ser. No. 552,983.

[51] Int. Cl.⁴ .............................................. A61F 9/00
[52] U.S. Cl. .................................. 128/303.1; 128/362
[58] Field of Search ...................... 128/303.1, 362, 395, 128/397, 398

[56] References Cited

U.S. PATENT DOCUMENTS 4,665,913  5/1987  L'Esperance ..................... 128/303.1

Primary Examiner—William E. Kamm
Assistant Examiner—David Shay
Attorney, Agent, or Firm—Hopgood, Calimafde, Kalil, Blaustein & Judlowe

[57] ABSTRACT

The invention contemplates removal of epithelium-layer material from the anterior surface of the cornea, as a step preparatory to sculpting laser surgery, wherein controlled ultraviolet irradiation of the cornea is operative to surgically ablate corneal tissue within an epithelium-free area which is in the optically used central region of the cornea. For corrective sculpting recurvatures involving relatively small diopter change, the sculpture proceeds via selectively distributed ultraviolet radiation to the epithelium-free area, with penetration essentially only or at least predominantly in the tissue of Bowman's membrane, thus achieving the corrected-curvature profile essentially only or predominantly in the tissue of Bowman's membrane.

10 Claims, 1 Drawing Sheet

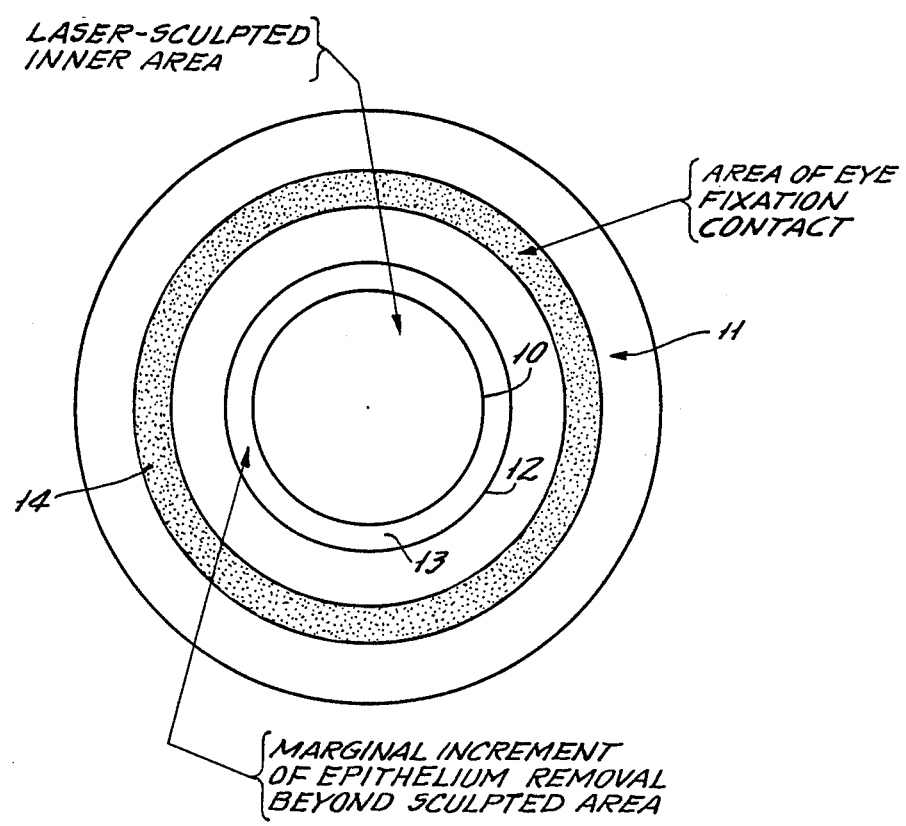

METHOD OF LASER-SCULPTURE OF THE OPTICALLY USED PORTION OF THE CORNEA

RELATED APPLICATIONS

This application is a continuation-in-part of application Ser. No. 049,333, filed May 13, 1987; and said application Ser. No. 049,333 is a continuation-in-part of pending applications Ser. No. 748,358, filed June 24, 1985, Pat. No. 4,665,913, Ser. No. 891,169, filed July 31, 1986, and Ser. No. 891,285, filed July 31, 1986, Pat. No. 4,732,148. Said application Ser. No. 748,358 is a continuation-in-part of original application Ser. No. 552,983, filed Nov. 17, 1983 (now abandoned). Said application Ser. No. 891,169 is a continuation-in-part of application Ser. No. 780,335, filed Sept. 26, 1985 (now abandoned); said application Ser. No. 780,335 is a continuation-in-part of application Ser. No. 740,276, filed June 3, 1985 (now abandoned); and said application Ser. No. 740,276 is a continuation of said original application. Said application Ser. No. 891,285 is a continuation-in-part of application Ser. No. 778,801, filed Sept. 23, 1985 (now abandoned); said application Ser. No. 778,801 is a continuation-in-part of application Ser. No. 742,225 filed June 6, 1985 (now abandoned); and said application Ser. No. 742,225 is a continuation-in-part of said original application. The disclosures of said applications are incorporated herein by reference.

BACKGROUND OF THE INVENTION

The invention relates to that aspect of ophthalmic surgery which is concerned with operations upon the external surface of the cornea.

Operations of the character indicated include corneal transplant and keratotomies; such operations have traditionally required skilled manipulation of a cutting instrument. But, however keen the cutting edge, the mere entry of the edge into the surface of the cornea necessarily means a wedge-like lateral pressure against body cells displaced by the entry, on both sides of the entry. Such lateral pressure is damaging to several layers of cells on both sides of the entry, to the extent impairing the ability of the wound to heal, and resulting in the formation of scar tissue.

My original patent application Ser. No. 552,983, filed Nov. 17, 1983, includes a background discussion of the effects of various available wavelengths of laser radiation in ophthalmic surgery and, in particular, surgery performed on the anterior surface of the cornea. It is explained that radiation at ultraviolet wavelengths is desirable by reason of its high photon energy. This energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breakdown of the intramolecular bonds. Photothermal and/or photocoagulation effects are neither characteristic nor observable in ablations at ultraviolet wavelengths, and cell damage adjacent the ablation is insignificant.

Said related-case applications deal with various concepts whereby laser radiation at ultraviolet wavelengths of 200-nm or less are controlled in delivery of laser radiation to the visually used area of the anterior surface of the cornea so as to penetrate the stroma and achieve a predeterminable volumetric removal of corneal tissue, thereby so correctively changing the profile of the anterior surface as to reduce a myopia, or a hyperopia, or an astigmatic abnormality which existed prior to such laser surgery.

Said related-case applications were concerned primarily with the methods and means of achieving desired corneal sculpture through controlled delivery of ultraviolet laser radiation. The disclosures of these applications were addressed to the ophthalmic surgeons who presumably are skilled in traditional procedures; but, although the laser-sculpting procedures I disclosed were contrary to current professional practice and beliefs, in the sense that I called for ablation depths which necessarily involved traversing Bowman's membrane in order to penetrate the stroma, I have been surprised that those skilled in laser technology who would attempt to experimentally apply my disclosures to their own research, have been unduly preoccupied with the epithelium, namely, the thin regrowable layer which nature provides for protection of the anterior surface of the cornea. I have found that such preoccupation with the epithelium can not only produce an undesirable result but can also be a reason for unpredictability of a desired result.

In my copending application Ser. No. 059,617, filed June 8, 1987, note is taken of the fact that the density of Bowman's membrane tissue, for which thickness is in the range from 10 to 15 microns, exceeds the density of underlying stroma, and a technique is described for achieving ablated recurvature of the anterior surface of the cornea by first making a uniform-depth penetration through Bowman's membrane, so that laser-sculpting action can proceed essentially only within stroma tissue. This procedure is effective, whatever the prescribed diopter change (i.e., for a relatively large range of diopter change), but of course it means that total corneapenetration depth must be the sum of the depth required to fully penetrate Bowman's layer, plus the stroma-penetration depth required for the particular prescription diopter change; for example, for a 5-mm diameter circular area which is to receive a two-diopter curvature change, the maximum penetration depth required for the recurvature is about 20 microns, and this must be added to the 15 microns required to assure uniform penetration through Bowman's membrane.

The present invention concerns itself with prescription diopter changes that require relatively small ablative penetration depths, as for example when the prescription area to be sculpted is of diameter less than 5-mm, or when only a one or two-diopter change is specified for a 5-mm diameter area.

BRIEF STATEMENT OF THE INVENTION

It is an object of the invention to provide improved procedure, before performing sculpturing laser surgery of the character indicated, whereby the laser surgery per se may be performed on a patient's cornea with greater confidence and assurance of achieving a given prescribed optically improved result.

A specific object is to perform, for prescription-diopter changes that are relatively small, curvature-correcting surgery on the anterior surface of the cornea by effecting the curvature-correcting profile essentially only or at least predominantly in Bowman's-membrane tissue.

It is also an object of the invention to achieve the above result with improved post-operative procedure which favors smooth and sufficient epithelium regrowth over the surgically affected region of the cornea.

Still another object is to achieve the foregoing objects with procedural steps which are within existing skills of the ophthalmic surgeon and which use materials with which such surgeons are familiar.

The invention achieves these objects by performing the pre-operative step of removing the epithelial layer from a central area of the cornea, wherein such removed area is slightly greater than the area to be subjected to ablation under ultraviolet laser radiation, whereby such laser action is directed to an epithelium-free area, namely, a direct exposure of Bowman's membrane; and then the relatively small diopter change in corneal curvature is achieved by so selectively delivering the ultraviolet radiation to the exposed stroma as to achieve a predetermined new curvature profile at least predominantly in the tissue of Bowman's membrane. Precaution is taken to avoid deleterious dehydration effects in the thus-exposed area, and the laser-sculpting procedure is accomplished, generally to a maximum penetration depth of less than 20 microns, and within 20 or 30 seconds. Post-operative procedure favorable to smooth and efficient epithelial regrowth over the surgically sculptured region is also described.

DETAILED DESCRIPTION

The invention will be described in detail in connection with the accompanying drawing which, on an enlarged scale, is a schematic view in front elevation of the anterior aspect of the cornea, with markings to permit descriptive identification of different significant areas involved in use of the invention.

As generally indicated above, the invention is concerned both with extra-operative procedural steps, and with the particular ultraviolet-irradiation procedure relied upon to selectively ablate the anterior surface of the cornea, with penetration essentially only or at least predominantly in Bowman's membrane, whereby to achieve such volumetric removal of corneal tissue as to correctively change an optically deficient pre-existing curvature to an optically improved new curvature. Illustrative description of such deficiencies and different techniques for their corrective improvement through selective irradiation from an ultraviolet laser, such as an argon-fluoride excimer laser, will be found in the above-noted pending applications and in those prior patent applications to which the pending applications bear a continuing or continuation-in-part relation; reference may therefore be had to said applications for detailed description.

An important extra-operative procedural step (i.e., prior to sculpture) is to locally remove epithelial-layer material from the anterior surface of the cornea as to assure no ultraviolet irradiation of the epithelium. For such assurance, this procedural step contemplates that epithelial-layer removal shall be throughout an area which continuously overlaps and surrounds the cornea-sculpting area of selective ablation via ultraviolet irradiation. If it is assumed that the cornea-sculpting area is a circle of 4 or 5-mm diameter, as could well be the case (a) for spherical-curvature reduction (to reduce a myopia condition) or (b) for spherical-curvature increase (to reduce a hyperopia condition) or (c) for cylindrical-curvature reduction (to reduce an astigmatism condition), then the area of epithelial-layer removal should be a circle which fully laps the cornea-sculpting area, preferably with a circumferentially continuous margin of about 1-mm incremental radius outside the circle of cornea-sculpting ablation. In the drawing, the circle 10 of cornea-sculpting action is seen in the central optically used portion of a cornea 11, and a preferred circle 12 of epithelial-layer removal is seen to be concentric with circle 10, thus providing a margin 13 of incremental radius outside circle 10, whereby to assure against epithelium exposure to ultraviolet irradiation.

When the area of circle 12 is epithelium-free, Bowman's membrane tissue is externally exposed. This membrane is relatively thin and shell-like, in that it is of density which differs from that of underlying stroma. In many cases, particularly for those involving 2 or more diopters of curvature change and a sculpted area of 5-mm or greater diameter, it is preferred first to perform uniform ablation of Bowman's membrane before performing ablative sculpture and that such sculpture be performed substantially only on stroma tissue; this is the procedure described in said copending application Ser. No. 059,617. But, for smaller-diopter prescription changes and/or for smaller-diameter prescription areas to be sculpted, a preference can be stated for accomplishing the recurvature sculpture essentially only with depth penetration of Bowman's membrane. Stated in other words, the involved sculpturing depth penetration should involve at least less penetration of the stroma than of Bowman's membrane. This being the case, the selective distribution of ultraviolet irradiation is such as to accomplish ablative sculpture of a new curvature substantially only by selective volumetric removal of the tissue of Bowman's membrane.

Preferred pre-operative (i.e., pre-surgery) procedural steps, in the illustrative context of circular areas delineated above and in the drawing, will appear from the following recital of specific steps and precautions which I have taken in laser-sculpting operation upon human patients to date:

1. With the patient lying on his back, with his head restrained to face straight up, and with retractors set to hold back upper and lower eyelids, a peri-bulbar or retro-bulbar anesthetic is administered to obtain anesthesia of the anterior portion of the eye and relative akinesia of the extra-ocular muscles.

2. A suction device or other means for outer-annulus steadying contact with the eye is applied to an area 14 having substantial radial offset from the area 12 within which epithelium is to be removed.

3. Within the inner limit of the area 14-steadying contact, the epithelium is kept in normally moist condition, by application to the cornea of one or more drops of an isotonic solution.

4. Having selected a scraping tool, such as a molded plastic spatula-like implement having a relatively narrow blade, e.g., having a 2 to 3-mm wide scraping edge of moderate sharpness, proceed to dislodge only epithelial-layer material from within the circle 12, the dislodged material being pushed to and temporarily accumulated upon the remaining undisturbed epithelial layer, namely, within the annular area outside circle 12 and within the inner limit of the area 14 of fixation contact.

5. The scraping dislodgement of epithelium may or may not be totally effective with the indicated scraper, but if more moisture is needed to wash away all epithelial material within area 12, another drop of the isotonic solution can be applied, and a dry cotton-tipped tooth pick (e.g., a so-called "Q-Tip") may be employed to sweep area 12 clear of all epithelial material, thus exposing a clean and smooth anterior aspect of Bowman's membrane, within area 12. The same or another "Q-Tip" device is then used to pick up and discard all of the accumulation of scraped epithelial material, from the outer annulus, i.e., from the area around circle 12. At all stages of performing steps 4 and 5, extreme caution is needed to assure against any scratching or other mechanical invasion of Bowman's membrane.

6. The patient is now conditioned for one of the laser-sculpting procedures selected from said pending patent applications, it being understood that prior to any of the above-described pre-surgery steps, the laser-delivery surgical apparatus will have been brought to a condition of instant readiness to perform a predetermined control of ultraviolet irradiation within the laser-sculpting area 10. Generally speaking, the laser-sculpting operation begins immediately after completion of epithelium removal, and when the area of circle 12 is smoothly denuded and epithelium-free; as explained above, this is preferably a procedure involving laser sculpture essentially only of Bowman's membrane tissue, with relatively little or no penetration of stroma tissue. Laser-sculpting proceeds to completion in less than one minute, e.g., about 20 seconds for a two-diopter spherical change of curvature with a 4-mm diameter area, in which case, there may in certain cases be no penetration of the stroma; on the other hand, for a two-diopter change over an area of 5-mm diameter, the depth of penetration is about 20 microns, which involves a relatively small fraction of depth penetration into the stroma.

7. Immediately upon termination of the laser surgery of step 6 above, the speculum or other eye-contacting retainer means is removed, and a solution significantly containing a cycloplegic agent is applied, as by one or more drops of the solution, to the area of surgical operation, to temporarily paralyze ciliary and iris musculature, thereby preventing spasm, irritation or other patient discomfort; and an antibiotic ointment, such as an erythromycin or chloromycetin ointment is applied to environmentally protect and cover the entire exposed area of the cornea.

8. The lids are then released and taped in closed condition, and a moderate-pressure bandage is applied over the taped lids, the bandage being configured so as not to allow the lids to separate.

9. The patient is then given a quiescent post-operative recuperative period of rest, for enhanced opportunity of epithelium regrowth into smooth and total coverage of the anterior surface of the cornea. Generally speaking, this epithelium regrowth proceeds to substantial completion in about 48 hours. But bandage removal and replacement, at 11 to 12-hour post-surgery intervals, is recommended, in order to track the expected progress of epithelium regrowth. The patient is released upon the surgeon's judgment that epithelium regrowth is complete.

In my surgical experience to date, involving use of one or more inventions of above-identified patent applications, I have used special apparatus designed and constructed by Taunton Technologies Inc., of Monroe, Conn. Said special apparatus is the subject of pending patent applications Ser. No. 938,633, filed Dec. 5, 1986 and Ser. No. 009,724, filed Feb. 2, 1987, as well as apparatus-divisional applications based on disclosures of one or more of the patent applications first identified above.

What is claimed is:

1. The method of improving optical properties of an eye by operating essentially only upon the optically used area of the anterior surface of the cornea of the eye, which method comprises a one-step procedure of tissue-ablating laser radiation of the anterior surface of the cornea in a volumetric removal of corneal tissue and with minimum depth penetration into the stroma and to a predetermined curvature profile, said step being one of selectively distributing the tissue-ablating radiation to exposed corneal tissue within said area to achieve the predetermined curvature profile essentially only by volumetric removal of Bowman's membrane tissue, and terminating said procedure upon achieving the predetermined curvature profile.

2. The method of changing the anterior surface of the cornea of an eye from an initial curvature in an optically used area having defective optical properties to a subsequent curvature having correctively improved properties to a subsequent optically used area, which method comprises:
 (a) removing only the epithelial layer from said area, whereby within said area Bowman's membrane is the externally exposed anterior surface of the cornea; and
 (b) then directionally and within said area impacting exposed corneal tissue with tissue-ablating laser irradiation to ablate predominantly Bowman's membrane tissue with volumetric removal of essentially only Bowman's membrane tissue to such penetration depth and prodile as to characterize the anterior surface of the cornea with said subsequent curvature.

3. The method of changing the anterior surface of the cornea of an eye from an initial curvature in an optically used area having defective optical properties to a subsequent curvature having correctively improved properties within said optically used area, which method comprises:
 (a) removing only the epithelial layer from said area, whereby within said area Bowman's membrane is the externally exposed anterior surface of the cornea; and
 (b) then directionally and within said area impacting exposed corneal tissue with tissue-ablating laser irradiation to ablate predominantly Bowman's membrane tissue with volumetric removal of Bowman's membrane tissue and of stroma tissue to such penetration depth as to characterize the anterior surface of the cornea with said subsequent curvature, the volumetric removal of Bowman's membrane tissue being substantially greater than the volumetric removal of stroma tissue.

4. The method of changing the anterior surface of the cornea of an eye from an initial curvature in an optically used area having defective optical properties to a subsequent curvature having correctively improved properties within said optically used area, which method comprises:
 (a) removing only the epithelial layer from said area, whereby within said area Bowman's membrane is the externally exposed anterior surface of the cornea; and
 (b) then directionally and within said area impacting exposed corneal tissue with tissue-ablating laser irradiation to ablate predominantly Bowman's membrane tissue with volumetric removal of Bowman's membrane tissue and of stroma tissue to such penetration depth as to characterize the anterior surface of the cornea with said subsequent curvature, the penetration depth into stroma tissue being less than the penetrated thickness of Bowman's membrane tissue.

5. The method of any one of claims 2, 3, 4 or 1, including the subsequent steps of applying an environmentally protective cover to said area and adjacent epithelium, and affording a quiescent post-operative period for epithelium regrowth over said area.

6. The method of improving optical properties of an eye by operating essentially only upon the optically used area of the anterior surface of the cornea of the eye, which method comprises a one-step procedure of ultraviolet radiation and attendant ablative photodecomposition of the anterior surface of the cornea in a volumetric removal of corneal tissue and with minimum depth penetration into the stroma and to a predetermined curvature profile, said step being one of selectively distributing the ultraviolet radiation to exposed corneal tissue within said area to achieve the predetermined curvature profile essentially only by volumetric removal of Bowman's membrane tissue, and terminating said procedure upon achieving the predetermined curvature profile.

7. The method of changing the anterior surface of the cornea of an eye from an initial curvature in an optically used area having defective optical properties to a subsequent curvature having correctively improved properties within said optically used area, which method comprises:
 (a) removing only the epithelial layer from said area, whereby within said area Bowman's membrane is the externally exposed anterior surface of the cornea; and
 (b) then directionally and within said area impacting exposed corneal tissue with ultraviolet irradiation to ablate predominantly Bowman's membrane tissue by photodecomposition with volumetric removal of essentially only Bowman's membrane tissue to such penetration depth and profile as to characterize the anterior surface of the cornea with said subsequent curvature.

8. The method of changing the anterior surface of the cornea of an eye from an initial curvature in an optically used area having defective optical properties to a subsequent curvature having correctively improved properties within said optically used area, which method comprises:
 (a) removing only the epithelial layer from said area, whereby within said area Bowman's membrane is the externally exposed anterior surface of the cornea; and
 (b) then directionally and within said area impacting exposed corneal tissue with ultraviolet irradiation to ablate predominantly Bowman's membrane tissue by photodecomposition with volumetric removal of Bowman's membrane tissue and of stroma tissue to such penetration depth as to characterize the anterior surface of the cornea with said subsequent curvature, the volumetric removal of Bowman's membrane tissue being substantially greater than the volumetric removal of stroma tissue.

9. The method of changing the anterior surface of the cornea of an eye from an initial curvature in an optically used area having defective optical properties to a subsequent curvature having correctively improved properties to a subsequent optically used area, which method comprises:
 (a) removing only the epithelial layer from said area, whereby within said area Bowman's membrane is the externally exposed anterior surface of the cornea; and
 (b) then directionally and within said area impacting exposed corneal tissue with ultraviolet irradiation to ablate predominantly Bowman's membrane tissue by photodecomposition with volumetric removal of Bowman's membrane tissue and of stroma tissue to such penetration depth as to characterize the anterior surface of the cornea with said subsequent curvature, the penetration depth into stroma tissue being less than the penetrated thickness of Bowman's membrane tissue.

10. The method of claim 2 or claim 3 or claim 4 or claim 1, including the subsequent steps of applying an environmentally protective cover to said area and adjacent epithelium, and affording a quiescent post-operative period for epithelium regrowth over said area.

* * * * *